(12) United States Patent
Puerta Llerena et al.

(10) Patent No.: US 9,163,069 B2
(45) Date of Patent: Oct. 20, 2015

(54) FUSION PROTEINS REPRESENTING DIFFERENT ALLERGENS AND A VACCINE AGAINST ALLERGY TO MITES

(71) Applicants: Leonardo Puerta Llerena, Cartagena (CO); Luis Caraballo, Cartagena (CO); José Fernando Cantillo, Cartagena (CO)

(72) Inventors: Leonardo Puerta Llerena, Cartagena (CO); Luis Caraballo, Cartagena (CO); José Fernando Cantillo, Cartagena (CO)

(73) Assignee: UNIVERSIDAD DE CARTAGENA (CO)

( * ) Notice: Subject to any disclaimer, the term of this patent is extended or adjusted under 35 U.S.C. 154(b) by 0 days.

(21) Appl. No.: 13/884,482

(22) PCT Filed: Sep. 20, 2012

(86) PCT No.: PCT/IB2012/054994
§ 371 (c)(1),
(2) Date: May 9, 2013

(87) PCT Pub. No.: WO2014/045084
PCT Pub. Date: Mar. 27, 2014

(65) Prior Publication Data
US 2014/0322257 A1    Oct. 30, 2014

(51) Int. Cl.
| C07K 5/00 | (2006.01) |
| C07K 14/435 | (2006.01) |
| A61K 39/35 | (2006.01) |
| A61K 39/00 | (2006.01) |

(52) U.S. Cl.
CPC ............ *C07K 14/43531* (2013.01); *A61K 39/35* (2013.01); *A61K 2039/70* (2013.01); *C07K 2319/00* (2013.01); *C07K 2319/21* (2013.01)

(58) Field of Classification Search
None
See application file for complete search history.

(56) References Cited

U.S. PATENT DOCUMENTS

| 7,862,828 B2 | 1/2011 | Linhart et al. |
| 2006/0233839 A1 | 10/2006 | Jacquet |
| 2007/0065468 A1 | 3/2007 | Chua et al. |
| 2008/0274059 A1 | 11/2008 | Moingeon et al. |
| 2009/0130130 A1 | 5/2009 | Chua et al. |
| 2011/0052640 A1 | 3/2011 | Asturias Ortega et al. |

FOREIGN PATENT DOCUMENTS

| WO | WO 2007/140505 | 12/2007 |
| WO | WO 2007/140505 A2 | 12/2007 |

OTHER PUBLICATIONS

European Search Report for EP 12870324 mailed Feb. 13, 2015 (3 pp).
Hales et al. "IgE and IgG anti-house dust mite specificities in allergic disease." *J Allergy Clin Immunol.* 118(2):361-367 (2006).
International Search Report for International Application No. PCT/IB2012/054994 mailed May 8, 2013 (2 pp).
Jimenez et al. "IgE Antibody Responses to Recombinant Allergens of Blomia tropicalis and Dermatophagoides pteronyssinus in a Tropical Environment." *Allergy Clin Immunol International* 19(6):233-238 (2007).
Llerna et al. "Sensitization to Bloma tropicalis and Lepidoglyphus destructor in Dermatophagoides spp-allergic individuals." *J. Allergy Clin. Immunol.* 88(6):943-950 (1991).
Zakzuk et al. "Evaluation of IgE responses against Blo t 8, a Glutathione S Transferase (GST) from Blomia tropicalis (Bt) mite." *J. Allergy Clin. Immunol.* 125(2):AB6 (2010).

*Primary Examiner* — Brian J Gangle
(74) *Attorney, Agent, or Firm* — Merchant & Gould P.C.

(57) ABSTRACT

The present invention refers to recombinant DNA molecules encoding fusion peptides from different allergens from *Blomia tropicalis* and *Dermatophagoides pteronyssinus* having potential usefulness in prevention and treatment of allergies caused by domestic mites. Specifically, the invention discloses fusion proteins comprising different fragments of allergens Der p 1, Der p 2, Der p 7, Der p 8, Blo t 5, Blo t 8, Blo t 18, Blo t 12 and Blo t 13 with reduced serum IgE reactivity in allergic and non-allergic individuals. It also discloses methods for production of these molecules in an expression system based on *E. coli* and purification. The invention refers also to effective and safe vaccines.

3 Claims, 6 Drawing Sheets

Primary sequence of recombinant PF3a

■ : Hist x 6

▢ : Blo t 5

▨ : Blo t 10

☰ : Blo t 12

▥ : Blo t 8

▢ : Blo t 13

▨ : Blo t 12

Primary sequence of recombinant PF14c

SEQUENCE LISTING

<160> NUMBER OF SEQ ID NOS: 4

<210> SEQ ID NO 1
<211> LENGTH: 592
<212> TYPE: PRT
<213> ORGANISM: Artificial Sequence
<220> FEATURE:
<223> OTHER INFORMATION: Synthetic sequence

<400> SEQUENCE: 1

```
Ala Thr Gly Gly Cys Ala Cys Ala Thr Cys Ala Cys Cys Ala Cys Cys
1 5 10 15

Ala Cys Cys Ala Thr Cys Ala Cys Gly Thr Gly Ala Ala Cys Ala Ala
20 25 30

Gly Ala Gly Cys Ala Ala Gly Gly Ala Ala Thr Thr Gly Cys Ala Ala
35 40 45

Gly Ala Gly Ala Ala Ala Ala Thr Cys Ala Thr Thr Cys Gly Ala Gly
50 55 60

Ala Ala Cys Thr Thr Gly Ala Thr Gly Thr Thr Gly Thr Thr Thr Gly
65 70 75 80

Cys Gly Cys Cys Ala Thr Gly Ala Thr Cys Gly Ala Ala Gly Gly Ala
85 90 95

Gly Cys Cys Cys Ala Ala Gly Gly Ala Gly Cys Thr Thr Thr Gly Gly
100 105 110

Ala Ala Cys Gly Thr Gly Ala Ala Thr Thr Gly Ala Ala Gly Cys Gly
115 120 125

Ala Ala Cys Thr Gly Ala Thr Cys Thr Thr Ala Ala Cys Ala Thr Thr
130 135 140

Thr Thr Gly Gly Ala Ala Cys Gly Ala Thr Thr Cys Ala Ala Cys Thr
145 150 155 160

Ala Cys Gly Ala Ala Cys Ala Ala Cys Gly Thr Gly Ala Gly Gly Ala
165 170 175

Ala Gly Cys Thr Thr Ala Thr Gly Ala Gly Cys Ala Ala Cys Ala Ala
180 185 190

Ala Thr Cys Cys Gly Ala Ala Thr Gly Ala Thr Gly Ala Cys Cys Gly
195 200 205

Gly Cys Ala Ala Gly Cys Thr Cys Ala Ala Gly Gly Ala Thr Thr Thr
210 215 220

Thr Ala Ala Thr Cys Thr Thr Thr Ala Thr Gly Ala Ala Thr Ala Thr
225 230 235 240

Thr Thr Gly Thr Gly Cys Cys Ala Thr Gly Thr Cys Ala Ala Gly Gly
245 250 255

Thr Gly Ala Thr Gly Gly Thr Gly Cys Cys Cys Gly Ala Ala Gly Thr
260 265 270

Gly Thr Thr Cys Gly Gly Thr Gly Ala Thr Thr Thr Thr Ala Ala Ala
275 280 285

Ala Thr Gly Ala Cys Thr Gly Ala Gly Thr Cys Ala Ala Gly Thr Ala
290 295 300

Gly Cys Ala Ala Thr Thr Thr Thr Gly Ala Ala Ala Cys Gly Ala Thr
305 310 315 320

Thr Ala Gly Ala Cys Gly Cys Ala Thr Thr Cys Cys Gly Thr Cys Ala
325 330 335

Thr Thr Ala Thr Gly Ala Thr Gly Gly Cys Cys Gly Ala Ala Cys Ala
340 345 350
```

-continued

```
Ala Thr Cys Ala Thr Thr Cys Ala Ala Cys Gly Cys Gly Ala Thr Gly
355 360 365

Thr Thr Cys Cys Cys Gly Gly Thr Ala Thr Cys Gly Ala Thr Cys Cys
370 375 380

Ala Ala Ala Thr Gly Cys Ala Thr Gly Cys Cys Ala Thr Thr Ala Thr
385 390 395 400

Ala Thr Gly Ala Ala Ala Thr Gly Thr Cys Cys Ala Thr Thr Gly Gly
405 410 415

Thr Thr Ala Ala Ala Gly Gly Ala Cys Ala Ala Cys Ala Ala Thr Ala
420 425 430

Thr Gly Ala Thr Ala Thr Thr Ala Ala Ala Thr Ala Thr Ala Cys Ala
435 440 445

Thr Gly Gly Ala Ala Thr Gly Thr Thr Cys Cys Ala Ala Ala Ala Ala
450 455 460

Thr Thr Gly Cys Ala Cys Cys Ala Ala Ala Ala Thr Cys Thr Gly Ala
465 470 475 480

Ala Ala Ala Thr Gly Thr Thr Gly Thr Cys Gly Thr Cys Ala Cys Thr
485 490 495

Ala Gly Thr Gly Ala Ala Gly Ala Thr Gly Gly Thr Gly Thr Thr Gly
500 505 510

Thr Cys Ala Ala Ala Gly Cys Thr Cys Ala Thr Thr Thr Gly Thr Thr
515 520 525

Gly Gly Thr Cys Gly Gly Thr Gly Thr Thr Cys Ala Thr Gly Ala Thr
530 535 540

Gly Ala Cys Gly Thr Thr Gly Thr Thr Thr Cys Ala Ala Thr Gly Gly
545 550 555 560

Ala Ala Thr Ala Thr Gly Ala Thr Thr Thr Ala Gly Cys Ala Thr Ala
565 570 575

Cys Ala Ala Ala Thr Thr Gly Gly Gly Thr Gly Ala Thr Thr Ala Ala
580 585 590

<210> SEQ ID NO 2
<211> LENGTH: 196
<212> TYPE: PRT
<213> ORGANISM: Artificial Sequence
<220> FEATURE:
<223> OTHER INFORMATION: Peptide fusion protein homologous to mite allergens

<400> SEQUENCE: 2

Met Ala His His His His His His Val Asn Lys Ser Lys Glu Leu Gln
1 5 10 15

Glu Lys Ile Ile Arg Glu Leu Asp Val Val Cys Ala Met Ile Glu Gly
20 25 30

Ala Gln Gly Ala Leu Glu Arg Glu Leu Lys Arg Thr Asp Leu Asn Ile
35 40 45

Leu Glu Arg Phe Asn Tyr Glu Gln Arg Glu Glu Ala Tyr Glu Gln Gln
50 55 60

Ile Arg Met Met Thr Gly Lys Leu Lys Asp Phe Asn Leu Tyr Glu Tyr
65 70 75 80

Leu Cys His Val Lys Val Met Val Pro Glu Val Phe Gly Asp Phe Lys
85 90 95

Met Thr Glu Ser Val Ala Ile Leu Lys Arg Leu Asp Ala Phe Arg His
100 105 110

Tyr Asp Gly Arg Thr Ile Ile Gln Arg Asp Val Pro Gly Ile Asp Pro
115 120 125
```

-continued

```
Asn Ala Cys His Tyr Met Lys Cys Pro Leu Val Lys Gly Gln Gln Tyr
    130                 135                 140

Asp Ile Lys Tyr Thr Trp Asn Val Pro Lys Ile Ala Pro Lys Ser Glu
145                 150                 155                 160

Asn Val Val Val Thr Ser Glu Asp Gly Val Val Lys Ala His Leu Leu
                165                 170                 175

Val Gly Val His Asp Asp Val Val Ser Met Glu Tyr Asp Leu Ala Tyr
            180                 185                 190

Lys Leu Gly Asp
        195

<210> SEQ ID NO 3
<211> LENGTH: 459
<212> TYPE: DNA
<213> ORGANISM: Artificial Sequence
<220> FEATURE:
<223> OTHER INFORMATION: Synthetic sequence

<400> SEQUENCE: 3
atggcacatc accaccacca tcacgtgaac aagagcaagg aattgcaaga gaaaatcatt     60
cgagaacttg atgttgtttg cgccatgatc gaaggagccc aaggagcttt ggaacgtgaa    120
ttgaagcgaa ctgatcttaa cattttggaa cgattcaact acgaacgtcg tattcaattg    180
atcgaagaag atttggaacg atcagaagaa cgacttaaaa ttgcaacagc taaattggaa    240
gaagcatcac aatctgccat aatatgttcc aaatctggtt cattgtggta cattaccgta    300
atgccatgtt cgattggaga ttttaaaatg actgagtcag tagcaatttt gaaacgacgt    360
agtttgagta cgttcgaagg tgacaacaag tttattcaca ccgaacccga tgatcatcac    420
gaaaagccaa cgacccagtg cacccatgag gagacatga                           459

<210> SEQ ID NO 4
<211> LENGTH: 152
<212> TYPE: PRT
<213> ORGANISM: Artificial Sequence
<220> FEATURE:
<223> OTHER INFORMATION: Peptide fusion protein homologous to mite
      allergens

<400> SEQUENCE: 4

Met Ala His His His His His His Val Asn Lys Ser Lys Glu Leu Gln
1               5                   10                  15

Glu Lys Ile Ile Arg Glu Leu Asp Val Val Cys Ala Met Ile Glu Gly
            20                  25                  30

Ala Gln Gly Ala Leu Glu Arg Glu Leu Lys Arg Thr Asp Leu Asn Ile
        35                  40                  45

Leu Glu Arg Phe Asn Tyr Glu Arg Arg Ile Gln Leu Ile Glu Glu Asp
    50                  55                  60

Leu Glu Arg Ser Glu Glu Arg Leu Lys Ile Ala Thr Ala Lys Leu Glu
65                  70                  75                  80

Glu Ala Ser Gln Ser Ala Ile Ile Cys Ser Lys Ser Gly Ser Leu Trp
                85                  90                  95

Tyr Ile Thr Val Met Pro Cys Ser Ile Gly Asp Phe Lys Met Thr Glu
            100                 105                 110

Ser Val Ala Ile Leu Lys Arg Arg Ser Leu Ser Thr Phe Glu Gly Asp
        115                 120                 125

Asn Lys Phe Ile His Thr Glu Pro Asp Asp His His Glu Lys Pro Thr
    130                 135                 140
```

-continued

```
Thr Gln Cys Thr His Glu Glu Thr
145                 150
```

FUSION PROTEINS REPRESENTING DIFFERENT ALLERGENS AND A VACCINE AGAINST ALLERGY TO MITES

This application is a National Stage Application of PCT/IB2012/054994, filed 20 Sep. 2012 and which application is incorporated herein by reference. To the extent appropriate, a claim of priority is made to the above disclosed application.

SEQUENCE LISTING

The present application includes a Sequence Listing in electronic format as a txt file entitled "Sequence-Listing", which was created on 9 May 2013 and is 9.31 KB (9,530 bytes) in size. The contents of txt file "Sequence-Listing" were filed electronically with the application on 9 May 2013 and are incorporated herein by reference.

TECHNICAL FIELD

The present invention relates to design of synthetic nucleotide sequences and to production of recombinant fusion proteins for treatment and prevention of allergies caused by domestic mites, in particular those caused by species *Blomia tropicalis* and *Dermatophagoides pteronyssinus*.

BACKGROUND OF THE INVENTION

Individuals allergic to domestic mites are in general sensitive to mites of genus *Dermatophagoides*, being *D. pteronyssinus* and *D. farinae* the most prevalent species worldwide. Additionally, in tropical and sub-tropical regions the presence of *B. tropicalis* is very abundant, being predominant sometimes in the population of mites present in house dust. In these regions, individuals allergic to mites are sensitive mostly to *D. pteronyssinus* and *B. tropicalis* (1).

About twenty allergens have been identified among domestic mites. However, only some of those have shown high reactivity frequency in the allergic population and some show cross-reactivity. Amongst *B. tropicalis* allergens, Blo t5 shows the highest reactivity frequency, Blo t12 and Blo t 13 show lower frequency, but induce an intense IgE in many of the sensitive individuals (2, 3).

Others as Der p1 and Der p2 are the most important *D. Pteronyssinus*, and between 50% and 100% of allergic individuals have IgE specific against these two allergens.

Another *D. Pteronyssinus* important allergen is Der p7, being estimated that 50% of individuals allergic to domestic mites shows IgE against this allergen. Allergens of mite groups 8 and 10, such as glutathione S transferase (GST) and tropomyosin, respectively, are of particular importance due to the significant crossed-reactivity observed with homologous derivate from different mite species and other organisms (4).

An allergen must produce cross-linking of IgE antibodies linked to the effector cells surface in order to induce cell activation and inflammatory response, requiring this process at least two IgE epitopes on the allergen surface. The IgE antibodies of an allergic patient may recognize continuous epitopes or discontinuous epitopes. Cross-linking of IgE antibodies on mast cells surface induce immediate release of biologically active mediators such as histamine and leukotrienes.

Decrease of allergenic capability can be achieved by intervention of IgE epitopes through mechanisms such as point mutation, amino acid deletion and disturbance of the natural molecular bending. Reordering amino acid segments conforming the primary sequence of the allergen also modifies the allergenic capability.

In some studies fusion or hybrid proteins have been generated to provide a better allergen-specific immunotherapy. Fusion proteins have been generated by using several portions of different allergens linked to form a unique molecule, intended to obtain vaccines poorly reactive to IgE antibody, which decreases the anaphylaxis risks, and to deliver to the patient only those allergens involved in development of allergic response (5).

A number of patents is known in this field related to pollen allergens (U.S. Pat. No. 7,862,828) and to domestic mites, as shown in documents US20080274059; US20110052640; US20070065468; US20060233839; US20090130130 and WO2007140505.

In fact, document U.S. Pat. No. 7,862,828 describes a method to prepare fusion allergens, consisting of two or more recombinant polypeptides from grass pollen, to be used as immunotherapeutic agent comprising: (a) to provide a polynucleotide sequence which codifies the fusion allergen, (b) to introduce said polynucleotide sequence into the host cell, (c) to grow the host cell to express the sequence, (d) to recover the fusion allergen expressed from the grown cell, (e) to assay the fusion allergen as a candidate for immunotherapy, by delivering the allergen to a test animal and to select those inducing the strongest immune response and generation of IgE blocking antibodies in comparison to that obtained with the individual components.

On this case, the polypeptide has at least two different allergenic proteins or their fragments. The hybrid polypeptide, the polynucleotide and the cell are useful for drug preparation for treatment of allergenic disorders or for prophylactic vaccination. Among allergenic sources for allergenic proteins, grass pollen, mites, bee venom or animal hair allergens may be the most important. Specific examples of allergenic proteins are group 1, group 2, group 4, group 5, group 6, group 11, group 12 and group 13 of allergens from the most important grass pollen, Der p 1 and Der p 2 (mites), phospholipase from bee venom, and Fel d 1 (cat).

On the other hand, document US20080274059 reveals fusion protein comprising a group 1 allergen and a group 2 allergen from genus *Dermatophagoides* fused at group 1 allergen N— o C—, where they may be Der p 1 or proDer p 1, and, from group 2, where they may be Der p 2. This document includes claims for the nucleic acid to develop the fusion protein, the expression cassette, the vector containing this cassette and a cell of any type including cassette or expression vector, and a vaccine composition including the fusion protein on a pharmaceutically acceptable support. The fusion protein is applied to prevent or treat allergic reactions to mites. The expression cell may be *Escherichia coli, Pichia pastoris* or *Saccharomyces cerevisiae*.

The United States Patent Application 20110052640 reports a hypoallergenic hybrid polypeptide comprising an amino acid sequence of at least 50 amino acids of a sequence selected from group 1 and 2 allergens from dust mites (*Dermatophagoides pteronyssinus*), and where a linkage epitope to IgE antibody of said allergen is deleted. Included are either the polypeptide having 70% sequence identity, the corresponding polynucleotide, the vector, the expression host cell including the polynucleotide, the method to produce the polypeptide and the pharmaceutical composition that comprises the polypeptide. The group 1 allergen is Der p 1, and that of group 2 is Der p 2. The obtained polypeptide keeps immunogenic capabilities, being particularly useful for allergy treatment. Additionally, production methods for these polypeptides in heterologous expression systems and efficient purification methods are described Patent US20070065468 reports a product for specific reduction of immunoglobulin E (IgE) as well as the allergic reaction, specifically a chimeric polypeptide having at least two mite allergens. It includes amino acid sequence for those allergens such as Der p 1, Der p 2 and Blo t 5. Allergens can be expressed in *Escherichia coli* or CHO—K1.

Patent US20060233839 describes a recombinant protein with an allergen derived from Der p1 where the protein has a reduced allergenic activity, important in relation to the allergen in natural state and comprising three mutation sites. In addition to Der p 1 allergen, ProDer p 1 and Der p 3 with ProDer p 3 and PreProDer p 3 are included. Claims include the nucleic acid molecule, the expression vector, the cell transformed for production of recombinant protein, and the immunological composition used for patient treatment.

Document US20090130130 refers to an isolated polypeptide, derivative or fragment composed by (a) a polypeptide, its derivate isoform, or a fragment thereof, comprising a non-helicoidal mutant of at least an allergen from group 5 mites and, (b) a polypeptide, its derivate isoform, or a fragment thereof comprising at least a substituted, added or deleted amino acid, or at least a chemical modification, where the polypeptide exhibits reduction in reactivity equal to or higher than IgE from the natural polypeptide, in subjects allergic to at least one allergen from group 5 mites. This polypeptide from the group 5 allergens may be Blo t 5, Der p 5, Der f 5, or Der m 5. Claims include nucleic acids sequences, a vector/host cell comprising nucleic acid molecules, a pharmaceutical preparation including the polypeptide or a vaccine.

Patent WO2007140505 reports a hypoallergenic protein comprising an allergen fused to or conjugated with at least a second non-allergenic protein or a fragment thereof. Included are claims for nucleic acid molecules encoding a hypoallergenic molecule or fusion protein, the vector, the host cell, an antibody addressed against the hypoallergenic or fusion protein, and the vaccine which may comprise it. The protein is derivate from Phl p 5, Fel d 1, Der p 2, Der p 7, Der p 21, Clone 30, Alt a 1, Par j 1, Ole e 1, Fel d 2, Can f 1, Can f 1, Art v 1, Amb a1, Alt a 2 or Alt a 6 having a terminal blunt in C- or N-terminus, and exhibiting reduced capability to IgE in comparison to native Phl p 5. The second protein is a viral, bacterial, fungal, or protozoan protein. For example, it is a virus capsid protein, preferably from picornaviridae.

Additionally, it is known that Linhart and collaborators (6) built, by PCR-based recombination, a fusion molecule composed by the most important allergens from timothy grass, in the order Phl p6, Phl p2, Phl p5 y Phl p1, which was expressed in *E. coli* as a 79 kDa protein. This molecule demonstrated to be useful for immunotherapy since it induced lymphoproliferation in a degree similar to that induced by a equimolar mix of the individual allergens in an model of mice allergic to pollen, induced Th1 and IgG profile cytokine production, able to block degranulation of mast cells incubated in the presence of the allergen.

The concept of fusion proteins has been also explored with mite allergens; a fusion protein composed by Der p1 and Der p2 portions showed lower IgE reactivity in comparison to native allergens and may induce mice to produce blocking IgG, which suggests their usefulness in immunotherapy (7).

Recently, Bussieres L. and collaborators (8) built several hybrid proteins composed by Der p1, Der p2 portions and a Der p1 precursor (pro-Der p1), showing that they are able to induce basophile degranulation in individuals allergic to domestic mites, and by "immunoblotting" with polyclonal and monoclonal antibodies, the conservation of B epitopes of native allergens was demonstrated.

Nevertheless, there is a non-satisfied need for vaccines based on recombinant molecules that contain several antigenic regions from mites common in tropical and subtropical areas, which may be suitable alternatives to immunotherapy schemes currently known, which are based on application of natural extracts from complete allergens, and which may be able to decrease the anaphylaxis risk and to improve the treatment efficacy.

DEFINITIONS

The terms used herein will have the following meanings:

"allergen", a substance able to induce an allergic reaction by inducing production of IgE antibodies.

"vaccine", a substance which can be used to stimulate the immune system to develop protection; the substance may be a polypeptide, such as the fusion protein subject of the present invention, in presence or absence of pharmaceutically acceptable carriers or vehicles.

"expression", refers to a gene or a gene product expression including the codified polypeptide.

DESCRIPTION OF THE DRAWINGS

FIG. 1. Schematic representation of peptides comprising the primary sequence of recombinant PF3a.

DETAILED DESCRIPTION OF THE INVENTION

The present invention is directed to fusion proteins with different allergen epitopes and reduced linking capability to IgE. The present invention is also directed to a pharmaceutical presentation allowing application within a cutaneous vaccination scheme ("Skin PrickTest"). The composition is: 1. Fusion protein, 2. Glycerol, and 3. Phenol.

The invention also reports synthetic nucleotide sequences design and production of recombinant fusion proteins for treatment and prevention of allergies caused by domestic mites, particularly caused by species *Blomia tropicalis* and *Dermatophagoides pteronyssinus*.

In other embodiment, the invention comprises nucleotide sequences artificially designed, codifying proteins related to domestic mites allergens.

The invention also refers to the design of two vectors based on vector pET45b+, the artificially designed nucleotide sequence being inserted such that a suitable reading frame is preserved, which expresses the recombinant protein with a histidine 6× tag, in the amino terminal region.

In this sense, the present invention is also addressed to vector pET-45b(+) which is a plasmid vector specifically ordered to Novagen, having a sequence that encodes a histidine 6x tag in the N-terminal region, followed by a sequence for a cleavage site by means of enzyme enterokinase and a sequence for a S-tag in the C-terminal region. It contains 5260 base pairs. The designed nucleotide sequence insertion was ordered for the fusion protein, PF3ao PF14c, at the position flanked by restriction sites Pml 1 and Kpn I, and such that a reading frame (ORF—Open ReadingFrame) was generated to express the protein of interest with nine additional amino acids in the N-terminal region under control of promoter T7. In this way, the invention reports a vector referred as pET45b/PF3a constituted by 5852 base pairs and a vector referred as pET45b/PF14c constituted by 5719 base pairs, which, when introduced into E. Coli bacteria, allow expression of recombinant proteins PF3a having 196 amino acids (SEQ ID NO: 2) and PF14 c having 152 amino acids (SEQ ID NO: 4), exhibiting the unique features disclosed in the present invention.

The invention also contemplates the possibility to combine, in a sole composition, the pharmaceutical formulation or vaccine including the two recombinant proteins making possible to improve or enhance their efficacy in immunotherapy against domestic mite allergy.

The vaccine for immunotherapy against domestic mite allergy according to the present invention is characterized by an amino acid sequence selected from the group consisting of SEQ ID NO: 2 and SEQ ID NO: 4 or a mixture thereof.

In still another embodiment, the invention refers to a method to obtain a recombinant fusion protein of different allergen segments from B. tropicalis expressed in Escherichia coli, which shows reactivity against IgE antibodies of an allergic population with lower frequency and intensity in comparison to that obtained from the allergenic extract from B. tropicalis.

Even another embodiment of the invention refers to a method to obtain a recombinant fusion protein having several allergen segments from B. tropicalis and D. Pteronyssinus, expressed in Escherichia coli, which shows reactivity against IgE antibodies of an allergic population with lower frequency and intensity in comparison to that obtained from the corresponding natural extracts.

The invention also refers to use of proteins designed according to the invention to prepare a medicament vaccine to treat an individual suffering allergies caused by domestic mites.

The invention is also addressed to a treatment method for an individual suffering allergies caused by domestic mites, which comprises administering to said individual a pharmaceutically effective amount of a protein according to the invention or a pharmaceutical composition containing the same.

Protein design according to the present invention starts with the selection of different allergens from domestic dust mites B. tropicalis and D. pteronyssinus, as well as of their antigen regions as reported in scientific publications or predicted by our bioinformatic analysis. The different selected regions were linked to form a unique primary protein structure. The probable 3D-structure for the designed protein was modeled from the amino acid sequence. The structure was optimized targeting to a successful expression as recombinant protein. In this manner, respective models were obtained for each of the two fusion proteins subject of the present invention.

Prediction for three-dimensional structure was performed by using I-TASSER (9) and Swiss-Model tools and software. (10, 11).

Segments combination and order producing a model satisfactory with regard to energy, stereochemistry and structure requirements were selected to order synthesis of an artificial nucleotide sequence encoding the primary sequence.

One vector was chosen for expression in E. Coli, i.e., pET 45b+ (NovagenR, catalog 71327-3), which was inserted in the artificial sequence to obtain a reading frame for expression of the encoded protein at the insertion site, with a histidine 6x tag in the N-terminal region, with no cleavage site to remove the tag.

The artificial gene synthesis with codon optimization for expression in bacteria, and its insertion in vector pET 45b+, such that a vector pET 45+b/PF was obtained for expression of fusion protein linked to the histidine 6× tag, was ordered to a US specialized company (GeneScript).

Once the artificial gene and the expression vector with insert were received, transformation was initiated in different E. Coli strains, according to the requirements of the protein of interest. The positive clones were selected after confirmation of the expected insert by PCR using universal primers, and expression was performed in LB (Luria-Bertani) medium, consistent of 1% tryptone, 0.5% yeast extract and 1% NaCl, pH 7.0, with antibiotic, IPTG (isopropyl-β-D-thiogalactoside) induction, one lactose analog, which acts as a protein expression regulator under lac operon control. Then, the culture was centrifuged for 10 minutes at 4000-6000 r.p.m., and the cell pellet was recovered. A standard procedure was followed (The Condensed Protocols from Molecular Cloning: A Laboratory Manual, Sambrook and Russel, CSHLPress), with modifications.

The cell pellet obtained was re-suspended in lysis buffer (NaH2PO4 100 mM, Tris-HCl 10 mM, Urea 8 M, pH 8.0) and stirred at 20 r.p.m. from one to two hours. The mixture was centrifuged 6000 r.p.m. for 10 minutes at 4° C., and the soluble fraction contained in the supernatant was recovered. 8 ml of this supernatant were mixed with Ni-NTA resin previously prepared by washing twice with water and balanced with lysis buffer, pH 6, and was stirred at 20 r.p.m. for two hours. The mixture was centrifuged at 1200-1600 r.p.m. for one minute, and the supernatant containing the fraction not linked to the resin was separated. The resin was washed several times with $NaH_2PO_4$ 20 mM, Urea 8 My NaCl 500 mM buffer solution at pH 8.0, 6.0 y 5.3 (2 washings at every pH). After every washing, the fraction not linked to the resin was separated by centrifugation at 1200-1600 r.p.m. for one minute and then discarded. The resin was loaded on a column and the fusion protein was recovered by application of a buffer elution solution ($NaH_2PO_4$ 20 mM, Urea 8 M, NaCl 500 mM at pH 4.0) to the column. Presence of the band of interest in the collected fractions was analyzed by electrophoresis on 15% poly-acrylamide under reductive conditions. Fractions were combined according to the intensity of the band of interest on the electrophoresis gel, and were diluted with the buffer elution solution.

To eliminate urea and induce protein re-naturalization, arginine-assisted oxidative re-naturalization was performed. In summary: fractions obtained and diluted after purification were dialyzed in dialysis bags having a 6-8000 kDa limit, against re-naturalization solution (100 mM Tris-HCl, 10 mM EDTA, 0.5 M L-Arginine, 5 mM Cysteine, 1 mM Cystine) at 1:20 ratio, under moderate and constant stirring overnight at 4° C. Then, dialysis was performed against 10 mM Tris-HCl, 0.1% TRITON® X-100 (t-octylphenoxypolyethoxyethanol) buffer solution for 4 hours with exchange at 2 hours. The re-naturalization products were analyzed by electrophoresis on 15% polyacrylamide under reduction conditions, and sorted at −20° C.

The linking capability of IgE and IgG antibodies on human sera was demonstrated by ELISA, electrotransfer, and immunodetection techniques, as per a procedure standardized in our laboratory.

The method disclosed in the present invention to obtain a recombinant protein from allergen segments of *B. tropicalis* (PF14c) and allergen segments of *B. tropicalis* and *D. pteronyssinus* (PF3a) expressed in *E. Coli*, with reactivity against IgE antibodies in allergic populations, with lower frequency and intensity in comparison to natural allergenic extracts from *B. tropicalis* and *D. Pteronyssinus*, comprises the following steps:

Transformation of *E. Coli* Cells:

Vector pET 45b(+)/PF containing the fusion protein segment of encoding nucleotides was used to transform competent One Shot® BL21 STAR™ (DE3) (Invitrogen, Cat. No. C6010-03) and TOP10 (Invitrogen Cat. No. C4040-10) *E. coli* cells, by means of a chemical treatment combined with thermal shock. In summary, 10 ng of vector were mixed and incubated with competent cells for 30 minutes on ice, followed by 30 seconds at 42° C. and then fast cooling on ice. To the foregoing mix, 250 μL of S.O.C optimized medium (consisting of 2% tryptone, 0.5% yeast extract, 10 mM NaCl, 2.5 mM KCl, 10 mM MgCl$_2$, 20 mM glucose) were added. Then, the mix was incubated at 37° C., 250 r.p.m. for 30 minutes. The mix was grown on LBA plates (Luria-Bertani, 1% tryptone, 0.5% yeast extract, 1% NaCl, pH 7.0, con ampicillin 100 mg/mL) at 37° C. overnight.

Selection of Transformed Colonies:

The presence of inserts in the transformed colonies was determined by PCR (Polymerase Chain Reaction) directly from the colonies, using the universal primers "T7 Promoter" and "T7 Terminator". For PCR, a reaction mixture was prepared as follows:

| | |
|---|---|
| DNA template (colony) 100 ng | 2 μL |
| dNTPs 50 mM | 1 μL |
| Primer "T7 terminator" (10 pmol) | 1 μL |
| Primer "T7 promoter" (10 pmol) | 1 μL |
| Buffer solution for PCR 10X | 5 μL |
| MgCl$_2$ 50 mM | 1.5 μL |
| Taq Polymerase 5 U/μL (Invitrogen, Cat. No. 116 15-010) | 1 uL |
| Deionized water | c.s.p. 50 μL |

Amplification schedule consisted of 30 cycles in three steps as follows: 1) 94° C. for one minute, 2) 50° C. for one minute, and 3) 72° C. for 2 minutes, with a 7-minute final extension at 72° C. The reaction was performed in a S-1000™ (BioRad) thermocycler. The amplification product was analyzed by electrophoresis on 2% agarose on a MINI-SUB® DNA Cell (BioRad) instrument at 50 volts. Positive clones were stored at −70° C. in 8% glycerol.

Expression of Fusion Protein:

The protein linked to the six-residue histidine tag (6xHis-tag) was obtained by induction with IPTG (isopropyl-β-D-thiogalactoside, a galactose analog, protein expression regulator under control of operon lac). Only one colony isolated from a culture of positive clone incubated on a LBA plate was grown on liquid LBA medium and incubated at 37° C., 250 r.p.m. for 12-14 hours. Then, the culture was diluted in liquid LBA (1:20 dilution) and incubated for 3-4 hours under same conditions until a OD600 (optical density at 600 nm) of 0.5-0.8 was accomplished, when IPTG was added and kept in induction for 3-6-hours at 37° C. Then, the culture was centrifuged for 10 minutes at 4000-6000 r.p.m. and the cell pellet was recovered. A standard procedure was followed (The Condensed Protocols from Molecular Cloning: A Laboratory Manual, Sambrook and Russel, CSHL Press), with modifications.

Purification and Re-Naturalization of Fusion Proteins:

The cell pellet obtained above was re-suspended in lysis buffer (100 mM NaH2PO4, mM Tris-HCl 10.8 M Urea, pH 8.0), stirred at 20 r.p.m. for 1-2 hours. The mix was centrifuged at 6000 r.p.m. for 10 minutes at 4° C., and the soluble fraction contained in the supernatant was recovered. 8 ml of this supernatant were mixed with the affinity resin based on Ni—NTA previously prepared by washing twice with water and balanced with lysis buffer, pH 6, and was stirred at 20 r.p.m. for two hours. The mixture was centrifuged at 1200-1600 r.p.m. for one minute, and the supernatant containing the fraction not linked to the resin was separated. The resin was washed several times with NaH2PO4 20 mM, Urea 8 M y NaCl 500 mM buffer solution at pH 8.0, 6.0 y 5.3 (2 washings at every pH). After every washing, the fraction not linked to the resin was separated by centrifugation at 1200-1600 r.p.m. for one minute and then discarded. The resin was loaded on a column and the fusion protein was recovered by application of a buffer elution solution (NaH2PO4 20 mM, Urea 8 M, NaCl 500 mM at pH 4.0) to the column. Presence of the band of interest in the collected fractions was analyzed by electrophoresis on 15% poly-acrylamide under reduction conditions. Fractions were combined according to the intensity of the band of interest on the electrophoresis gel, and were diluted with the buffer elution solution.

To eliminate urea and induce protein re-naturalization, arginine-assisted oxidative re-naturalization was performed. In summary: fractions obtained and diluted after purification were dialyzed in dialysis bags having a 6-8000 kDa limit, against re-naturalization solution (100 mM Tris-HCl, 10 mM EDTA, 0.5 M L-Arginine, 5 mM Cysteine, 1 mM Cystine) at 1:20 ratio, under moderate and constant stirring overnight at 4° C. Then, dialysis was performed against 10 mM Tris-HCl, 0.1% TRITON® X-100 (t-octylphenoxypolyethoxyethanol) buffer solution for 4 hours with exchange at 2 hours. The re-naturalization products were analyzed by electrophoresis on 15% polyacrylamide under reduction conditions, and were stored at −20° C.

Figure 1:
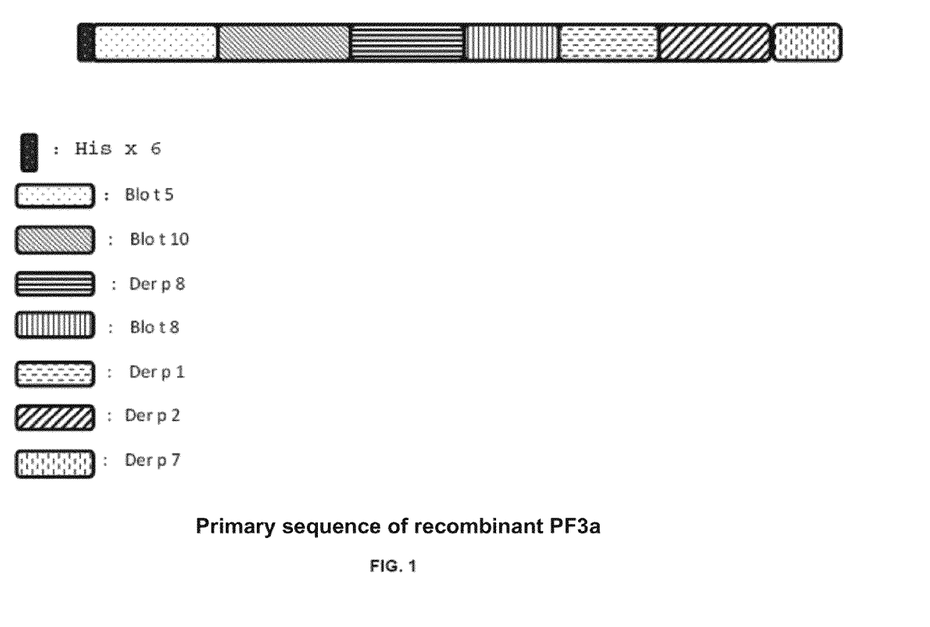
Figure 2:
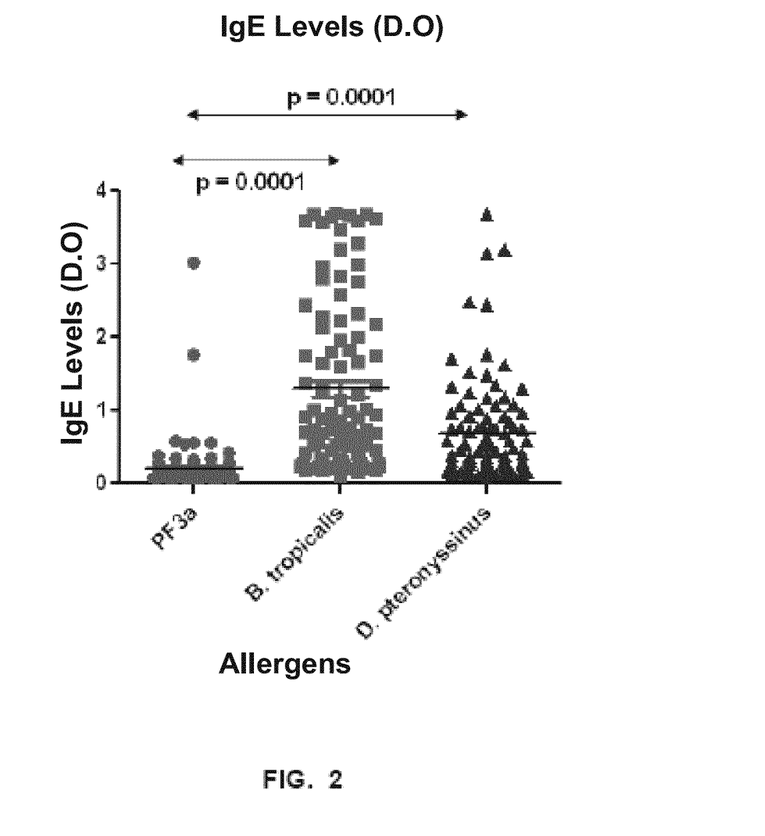
FIG. 2. Levels of serum IgE specific for PF14c determined by ELISA, in comparison to reactivity levels of natural extracts from *B. tropicalis* and *D. pteronyssinus*.

Features of Recombinant Proteins:

PF3a:

It is the protein corresponding to SEQ ID NO:2 and comprises 196 amino acids corresponding to different fragments contained in allergens from mites *Blomia tropicalis* and *D. pteronyssinus*; Blo t 5 (Accession Number:O96870.1, GI:14423644 and 2 JRKA GI:193506481), Der p 2 (Accession Number:P49278.1, GI:1352237), Blo t 10 (Accession Number ABU97466.1, GI:156938889), Der p 8 (Accession Number P46419.1, GI:1170095), Blo t 8 (ACV04860.1,GI: 256665455) Der p 1 (Accession Number ACG58378.1, GI:195933901), Der p 2 (Accession Number P49278.1, GI:1352237 and Der p 7 (Accession Number 3H4Z-AGI: 292659601). This protein with a 196 amino acid sequence, 22.8 KD, has allergenic segments from allergens from mites *Blomia tropicalis* and *Dermatophagoides pteronyssinus*.

Figure 3:
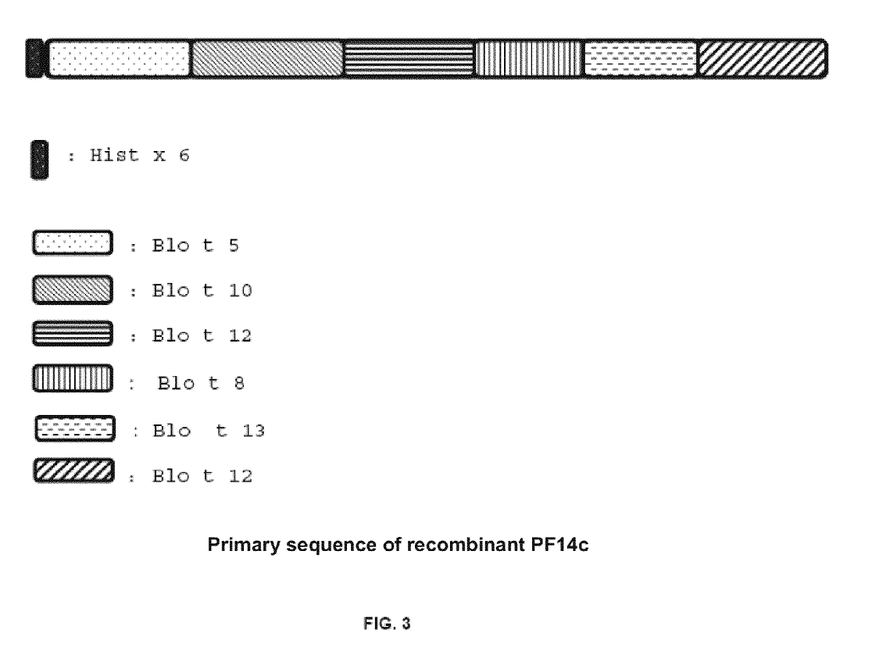
FIG. 3. Schematic representation of peptides comprising the primary sequence of recombinant PF14c.
Figure 4:
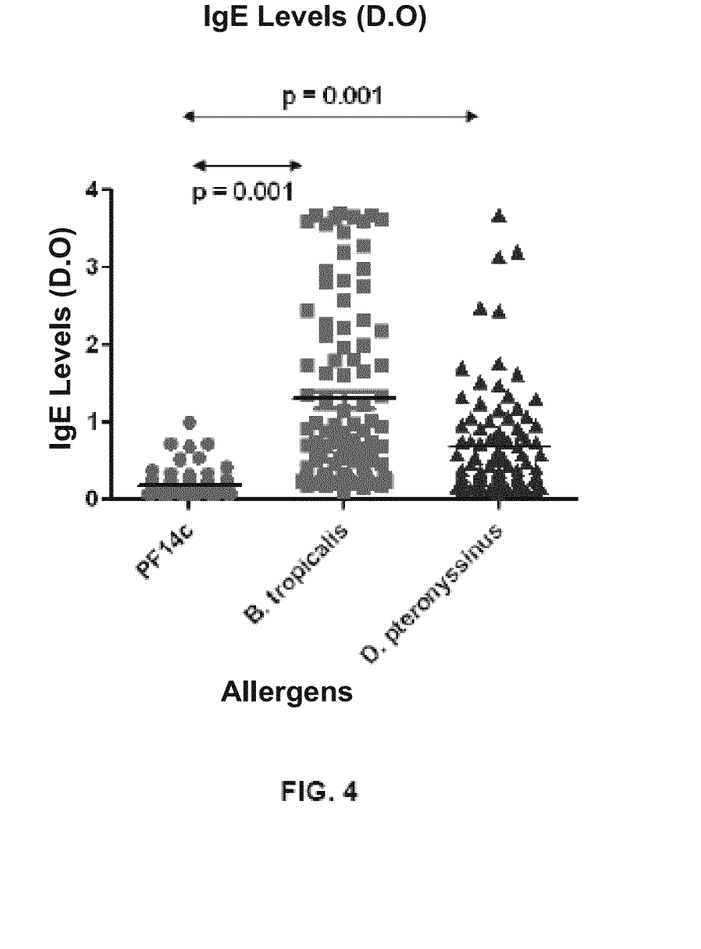
FIG. 4. Levels of serum IgE specific for PF14c determined by ELISA in comparison to reactivity levels of natural extracts from *B. tropicalis* and *D. pteronyssinus*.
Figure 5:
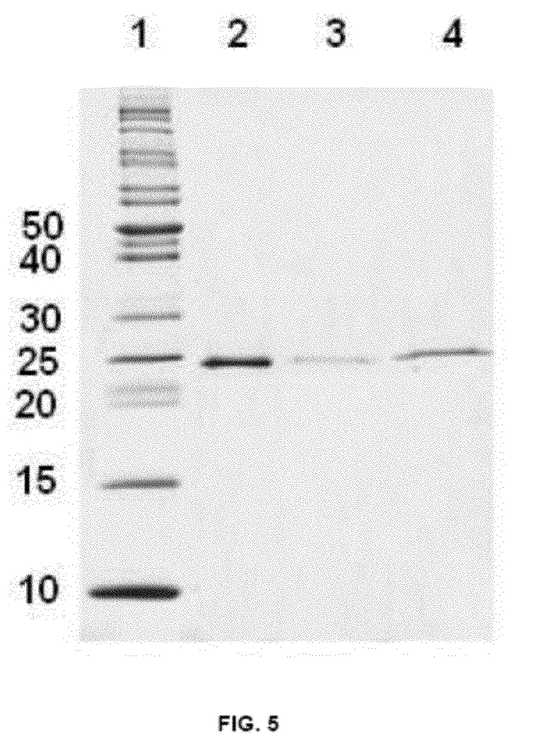
FIG. 5. Purification profile for PF3a performed by gel electrophoresis on 15% polyacrylamide, stained with Comassie Blue. 1 is the molecular weight marker, 2 and 3 correspond to non-dialyzed samples, and 4 corresponds to the dialyzed sample in 0.1% TRITON® X-100 (t-octylphenoxypolyethoxyethanol) buffer.
Figure 6:
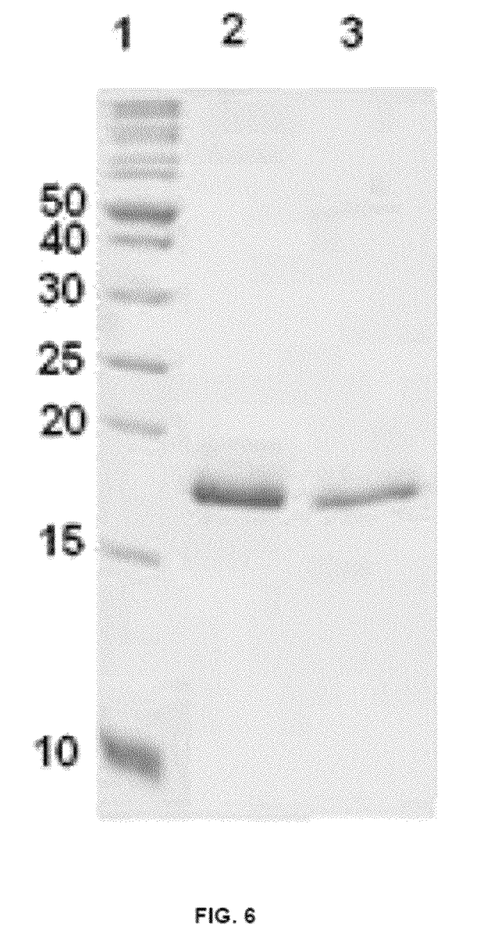
FIG. 6. Purification profile for PF14c performed by gel electrophoresis on 15% polyacrylamide, stained with Comassie Blue. Lane 1 is the molecular weight marker, 2 and 3 represent the purified fractions.

PF14c:

This is the protein corresponding to SEQ ID NO: 4, comprising 152 amino acids corresponding to different fragments found in 6 allergens from mite *Blomia tropicalis*, Blo t 5 (Accession Number: ABH06352.1, GI:111120436), Blo t 8 (ACV04860.1, GI: 256665455) Blo t 10 (Accession Number ABU97466.1, GI: 156938889), Blo t 12 (Q17282.1, GI: 2498195) and Blo t 13 (Q17284.1, GI:14423698). This 152 amino acid protein, 17.8KD, has allergenic segments from allergens from mite *Blomia tropicalis*.

The invention claimed is:

1. A recombinant protein comprising the amino acid sequence of SEQ ID NO: 2 or SEQ ID NO: 4, wherein said amino acid sequence SEQ ID NO:2 is encoded by nucleotide sequence SEQ ID NO: 1, and wherein said amino acid sequence SEQ ID NO:4 is encoded by nucleotide sequence SEQ ID NO: 3.

2. A vaccine against domestic mite allergy comprising a recombinant protein comprising an amino acid sequence selected from the group consisting of SEQ ID NO: 2 and SEQ ID NO: 4.

3. A vaccine against domestic mite allergy comprising a recombinant protein comprising amino acid SEQ ID NO: 2 and amino acid SEQ ID NO: 4.

* * * * *